US00PP16606P3

(12) United States Plant Patent
van der Voort

(10) Patent No.: US PP16,606 P3
(45) Date of Patent: Jun. 6, 2006

(54) LILY PLANT NAMED 'BERNINI'

(50) Latin Name: *Lilium L.*
Varietal Denomination: Bernini

(75) Inventor: Cees A. van der Voort, Katwijk (NL)

(73) Assignee: Vletter & Den Haan Beheer B.V., Rijnsburg (NL)

( * ) Notice: Subject to any disclaimer, the term of this patent is extended or adjusted under 35 U.S.C. 154(b) by 0 days.

(21) Appl. No.: 09/357,103

(22) Filed: Jul. 19, 1999

(65) Prior Publication Data

US 2002/0059670 P1 May 16, 2002

(51) Int. Cl.
*A01H 5/00* (2006.01)

(52) U.S. Cl. ..... Plt./315
(58) Field of Classification Search ..... Plt./315
See application file for complete search history.

(56) References Cited

PUBLICATIONS

UPOV–ROM GTITM Computer Database 2000/02, GTI Jouve Retrieval Software, citation for 'Bernini', 1993.* http://www.user.netland.nl/~hanns//exit4.html, p. 2, May 1996.* http://www.user.netland.nl/~hanns//exit4.html, Aalsmeer Horticultural Sites, pp. 1–6, see p. 2, citation for 'Bernini', May 5, 1996.*

UPOV–ROM GTITM Computer Database 2000/02, GTI Jouve Retrieval Software, citations for 'Bernini'.*

* cited by examiner

*Primary Examiner*—Anne Marie Grunberg
(74) *Attorney, Agent, or Firm*—Foley & Lardner, LLP

(57) ABSTRACT

A new and distinct cultivar of Lily plant named 'Bernini' characterized by having large, upright, pink flowers, curled axis of the outer tepals, dark-pink spots on the tepals, and vigorous growth habit.

1 Drawing Sheet

BACKGROUND OF THE INVENTION

The present invention comprises a new and distinct cultivar of lily plant, botanically known as *Lilium L.*, and hereinafter referred to by the cultivar name 'Bernini'.

'Bernini' is a product of a planned breeding program which had the objective of creating new lily cultivars having large, upright, pink flowers.

'Bernini' was originated from a hybridization made by the inventor in a controlled breeding program in Rijnsburg, the Netherlands, in 1983. The male and female parents were unnamed seedlings of *Lilium L.* oriental hybrids. Both parents are proprietary cultivars used in the breeding program.

'Bernini' was discovered and selected as one flowering plant within the progeny of the stated cross by the inventor, Cees A. van der Voort, on Jun. 7, 1983 in a controlled environment in Rijnsburg, the Netherlands.

The first act of asexual reproduction of 'Bernini' was accomplished when scales were taken from the initial selection in October 1986 in a controlled environment in Rijnsburg, the Netherlands by, or under the supervision of, Cees A. van der Voort. Horticultural examination of selected units initiated in May, 1986 has demonstrated that the combination of characteristics as herein disclosed for 'Bernini' are firmly fixed and are retained through successive generations of asexual reproduction.

BRIEF DESCRIPTION OF THE INVENTION

The following traits have been repeatedly observed and are determined to be basic characteristics of 'Bernini' which, in combination, distinguish this lily as a new and distinct cultivar:

1. large, upright, pink flowers;
2. curled axis of the outer tepals;
3. dark-pink spots on the tepals; and
4. vigorous growth habit.

'Bernini' has not been observed under all possible environmental conditions. The phenotype of the new cultivar may vary significantly with variations in environment such as temperature, light intensity, and daylength without any change in genotype. The following observations, measurements, and comparisons describe plants grown in the Dutch experimental research station CPRO-DLO, Wageningen, the Netherlands under conditions which approximate those generally used in commercial practice.

Of the many commercial cultivars known to the present inventor, no other cultivars are similar in comparison to 'Bernini'.

BRIEF DESCRIPTION OF THE DRAWING

The accompanying color photographic drawing shows typical plant and flower characteristics of 'Bernini', with colors being as true as possible with illustrations of this type.

DETAILED BOTANICAL DESCRIPTION

In the following description, color references are made to The Royal Horticultural Society Colour Chart (R.H.S.). The color values were determined between 12 am and 2 pm at the Dutch experimental research station CPRO-DLO, Wageningen, the Netherlands.

Origin: Seedling from breeding program.

Parentage:

*Female parent*.—Unnamed seedling.

*Male parent*.—Unnamed seedling.

Classification:

*Botanical*.—A hybrid of the genus *Lilium L.*

*Commercial*.—Oriental Lily cv. 'Bernini'.

Plant:

*Form*.—A single stem carrying numerous, alternately arranged pedicels.

*Height*.—Medium to high for the mature plant, approximately 120 cm.

*Growth habit*.—Vigorous; from the beginning of vegetation to the first flowering takes 90 days, depending on cultivation conditions, especially temperature i.e., approximately 20–30% more vigorous than the traditional 'Stargazer' cultivar.

*Stem*.—Circular in transverse section; anthocyanin pigmentation absent; internodal length 6.5 cm, depending on the cultivation conditions of the cultivar.

*Foliage*.—Quantity: Approximately 70, depending on cultivation conditions. Size of leaf: Mature leaves are approximately 11 cm long and 3.5 cm wide. Shape of leaf: Generally ovate. Color: Light green, RHS 136B.

*Bulb*.—Size: 16 to 18 cm in circumference. Color: White RHS 157B with pink shades.

Bud:

*Form*.—Tapering like a lancet.

*Size*.—12 cm in length depending on cultivation conditions.

*Opening*.—Unfolds normally.

*Color*.—Pink, RHS 64D, with greyed-green accents, RHS 194D.

*Tepals*.—Folded, three visible.

Flower:

*Blooming habit*.—Raceme.

*Size*.—Large, 23 cm in diameter depending on cultivation conditions.

*Borne*.—Upright along a longitudinal axis.

*Shape*.—Generally, hexagonal star in form and bowl-shaped in cross-section.

*Tepalage*.—Number of Tepals: 6. Arrangement: Three inner and three outer. Color: Upper Surface: Pink, RHS 63B to RHS 86B, flower mid-vein RHS 63A. Lower Surface: Pink, RHS 65A. Spotting or Marking: Spots and markings are present, dark pink in color, RHS 68A.

*Pedicel*.—Length: 8.5 cm, depending on the cultivation of the cultivar. Color: RHS 132D. Form: Rounded.

*Texture*.—Papillose.

*Disease resistance*.—Average in comparison to the disease resistance level of traditional Lily cultivars.

*Fragrance*.—Weak.

*Lasting quality*.—Excellent; i.e., the average lasting period is at least 21 days, when cut and kept in a controlled climate in conformity with Dutch Auctions and Research Station standards.

Reproductive organs:

*Stamens and anthers*.—Arrangements: Anthers form a generally circular pattern at their upper ends. Number: 6. Length: Long, depending on cultivation conditions. Filaments Color: RHS 145D, yellow-green.

*Pollen color*.—Greyed-red, RHS 180B.

*Anther color*.—Reddish brown RHS 180B.

*Pistils*.—Green RHS 145B.

*Stigma*.—Greyed-purple RHS 187A.

*Ovaries*.—Triangular in shape.

I claim:

1. A new and distinct cultivar of Lily plant named 'Bernini', as illustrated and described herein.

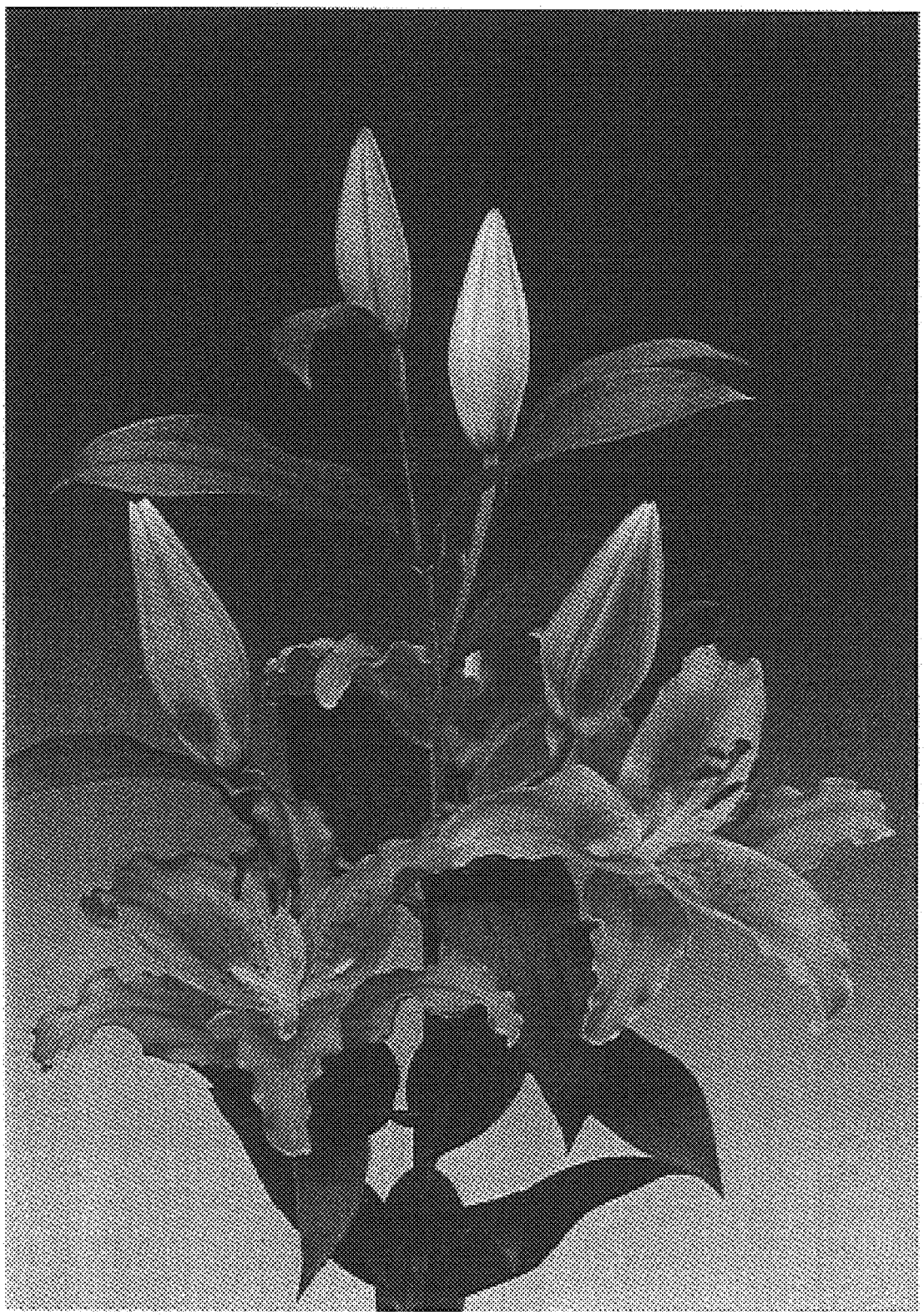

* * * * *